US011980442B2

United States Patent
Ortega-Quijano et al.

(10) Patent No.: US 11,980,442 B2
(45) Date of Patent: *May 14, 2024

(54) DEVICE FOR THE DISCRIMINATION OF BIOLOGICAL TISSUES

(71) Applicant: Deneb Medical, S.L., San Sebastián (ES)

(72) Inventors: Noé Ortega-Quijano, San Sebastián (ES); Nebai Bernal Simón, San Sebastián (ES); Iñigo Olcoz Basarte, San Sebastián (ES); Juan Arregui Altuna, San Sebastián (ES); Aritz Lazkoz Del Campo, San Sebastián (ES); José Antonio Aguilera Andoaga, San Sebastián (ES); Carlos Aragón Garbizu, San Sebastián (ES)

(73) Assignee: Deneb Medical, S.L. (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/730,611

(22) Filed: Apr. 27, 2022

(65) Prior Publication Data

US 2022/0265147 A1   Aug. 25, 2022

Related U.S. Application Data

(63) Continuation of application No. 16/240,215, filed on Jan. 4, 2019, now Pat. No. 11,344,201.

(30) Foreign Application Priority Data

Mar. 1, 2018 (EP) .................................... 18382130

(51) Int. Cl.
  *A61B 5/00* (2006.01)
  *A61B 34/00* (2016.01)
  (Continued)

(52) U.S. Cl.
  CPC .......... *A61B 5/0075* (2013.01); *A61B 5/0084* (2013.01); *A61B 34/00* (2016.02);
  (Continued)

(58) Field of Classification Search
  None
  See application file for complete search history.

(56) References Cited

U.S. PATENT DOCUMENTS 9,383,260 B1   7/2016 Yoo et al.
2002/0149768 A1   10/2002 Sabsabi et al.
(Continued)

FOREIGN PATENT DOCUMENTS

WO   2011035792 A1   3/2011
WO   2017025335 A1   2/2017
(Continued)

OTHER PUBLICATIONS

Yueh et al., "Preliminary evaluation of laser-induced breakdown spectroscopy for tissue classification" Spectrochimica Acta Part B 64 (2009) 1059-1067 (Year: 2009).*

(Continued)

*Primary Examiner* — Colin T. Sakamoto
(74) *Attorney, Agent, or Firm* — Lerner David LLP

(57) ABSTRACT

The present invention relates to a device for the discrimination of biological tissues, such that it is capable of carrying out the discrimination of tissue under complicated operating conditions, for example due to the presence of contaminating elements given off by a cutting operation, due to the presence of moisture in the biological tissue, or due to the presence of a non-controlled atmosphere that interferes with the results of the readings. The invention allows building more complex devices, including cutting instruments, such that it is possible to carry out a surgical (Continued)

intervention in a safe manner by preventing cutting into tissues that are to be avoided during said cutting operation.

12 Claims, 6 Drawing Sheets

(51) Int. Cl.
| | |
|---|---|
| A61B 90/00 | (2016.01) |
| G01J 3/02 | (2006.01) |
| G01J 3/44 | (2006.01) |
| G01N 21/71 | (2006.01) |
| G16C 99/00 | (2019.01) |
| A61B 17/00 | (2006.01) |

(52) U.S. Cl.
CPC ............ *A61B 90/04* (2016.02); *G01J 3/0218* (2013.01); *G01J 3/0248* (2013.01); *G01J 3/44* (2013.01); *G01N 21/718* (2013.01); *G16C 99/00* (2019.02); *A61B 2017/00061* (2013.01); *G01N 2201/129* (2013.01)

(56) References Cited

U.S. PATENT DOCUMENTS

| | | |
|---|---|---|
| 2005/0200843 A1 | 9/2005 | Kumar et al. |
| 2012/0010603 A1 | 1/2012 | Milner et al. |
| 2012/0165727 A1 | 6/2012 | Campbell et al. |
| 2012/0245509 A1 | 9/2012 | Tran et al. |
| 2014/0085631 A1 | 3/2014 | Lacour et al. |
| 2016/0084709 A1 | 3/2016 | Day et al. |
| 2016/0334336 A1 | 11/2016 | Aguilera Andoaga et al. |
| 2017/0023484 A1 | 1/2017 | Wang et al. |
| 2017/0067782 A1 | 3/2017 | Wang et al. |
| 2017/0074800 A1 | 3/2017 | Benmansour et al. |
| 2017/0082549 A1 | 3/2017 | Washburn |
| 2017/0191940 A1 | 7/2017 | Sabsabi et al. |
| 2017/0196444 A1* | 7/2017 | Pyun ................ A61B 5/6847 |
| 2019/0033231 A1 | 1/2019 | Connell et al. |
| 2019/0267221 A1 | 8/2019 | Pringle et al. |
| 2020/0182795 A1 | 6/2020 | Blouin et al. |

FOREIGN PATENT DOCUMENTS

| | | |
|---|---|---|
| WO | 2017212248 A1 | 12/2017 |
| WO | 2018115415 A1 | 6/2018 |

OTHER PUBLICATIONS

Mehari et al., "Laser-induced Breakdown Spectroscopy (LIBS) based tissue type mapping of ex-vivo soft tissues—A prospect for tissue specific Laser surgery" Optics in the Life Sciences Congress, OSA Technical Digest (online) (Optica Publishing Group, 2017), paper JS1A.2 (Year: 2017).*

Yoshikawa et al., "Clinical application of projection of mapping technology for surgical resection of lung metastasis" Interactive CardioVascular and Thoracic Surgery 25 (2017) 1010-1011 (Year: 2017).*

Regeling et al., "Hyperspectral Imaging Using Flexible Endoscopy for Laryngeal Cancer Detection" Sensors 2016, 16, 1288 (Year: 2016).*

Fanuel Mehari et al.: "LIBS based Tissue Differentiation for Er: YAG Surgical Laser", Proceedings of the 6th International conference on photonics, optics and laser technology, 2018.

Sancey L, Motto-Ros V, Busser B, Kotb S, Benoit JM, Piednoir A, Lux F, Tillement O, Panczer G, Yu J. Laser spectrometry for multi elemental imaging of biological tissues. Scientific reports. Aug. 14, 2014;4:6065. 7 pages.

International Search Report for PCT/EP2019/054970 dated Mar. 29, 2019; 3 pages.

Son et al., "Application of Pulsed Buffer Gas Jets for the Signal Enhancement of Laser-Induced Breakdown Spectroscopy" Applied Spectroscopy, vol. 64, Issue No. 11, pp. 1289-1297, Nov. 2010 (Year: 2010).

* cited by examiner

DEVICE FOR THE DISCRIMINATION OF BIOLOGICAL TISSUES

CROSS-REFERENCE TO RELATED APPLICATIONS

The present application is a continuation of U.S. application Ser. No. 16/240,215, which claims priority from European Patent Application No. EP18382130.5, filed Mar. 1, 2018, the disclosure of which is hereby incorporated herein by reference.

OBJECT OF THE INVENTION

The present invention is a device for the discrimination of biological tissues, such that it is capable of carrying out the discrimination of tissue under complicated operating conditions, for example due to the presence of elements produced by a cutting operation, due to the presence of moisture in the biological tissue, or due to the presence of a non-controlled atmosphere that may interfere with the results of the readings.

The invention allows building more complex devices, including cutting instruments, such that it is possible to carry out a surgical intervention in a safe manner by preventing cutting into tissues that are not to be damaged during said cutting operation.

BACKGROUND OF THE INVENTION

The object of the invention is the distinction of biological tissues under actual clinical conditions, particularly based on LIBS (Laser-Induced Breakdown Spectroscopy). This technology consists of making a highly energetic excitation laser beam (typically an Nd:YAG (neodymium-doped yttrium aluminum garnet) pulsed laser) strike a material under study (in this case the tissue), suitably focusing it if needed, which produces an ionization of the material on the microscopic level that generates a plasma plume.

Said plasma emits light radiation the characteristic spectrum (light intensity emitted for each wavelength) of which depends directly on the chemical composition of the material. Therefore, the measurement and analysis of the spectrum of the plasma allows knowing the chemical composition of the sample under study and therefore allows deducing what type of material it is. Different types of materials in general, and biological tissues in particular can thereby be distinguished.

One of the most important problems of this technique when it is used under clinical conditions arises due to moisture and also due to elements that are not related to the tissue, such as elements produced by a cutting operation, on the surface of the material the laser strikes or in the surrounding atmosphere, the presence of which makes the appearance and/or the correct measurement of the spectrum emitted by the plasma difficult.

Under these circumstances, the plasma may not be produced, or the plasma is produced but the measured spectrum corresponds to both the biological tissue and the elements that are not related to the tissue, distorting the readings and leading to conclusions that may be incorrect or even dangerous if decisions such as whether or not to cut the biological tissue depend on such readings.

One of the first causes of the presence of moisture or liquid media is the presence of water that is intrinsically contained in biological tissues; the blood supply, primarily in those tissues that are highly vascularized, such as the liver and kidneys; and the presence of other body fluids, such as, for example, cerebrospinal fluid, and other body fluids such as saliva, bile, semen, urine, or mucus (present in the respiratory tract, digestive tract, reproductive tract, nasal tract, and others).

In addition to the aforementioned difficulties are those relating to the case in which the device can work when used in a clinical context. Among such difficulties the following examples are distinguished:

Presence of Non Bodily Aqueous Medium

During surgery, there may be a presence of external liquids. The clearest example is the saline flow that is typically used for irrigation in order to clean the surgical field in general, and to reduce the heat generated by laser cutting and thereby prevent burning in particular.

With the use of a cutting laser, the application of a saline flow is essential in order to dissipate the thermal effects associated with cutting. This flow represents an additional difficulty along with the intrinsic moisture of the tissues being acted on, since it prevents the generation of plasma in some cases and the reduction of the intensity of the plasma generated in others.

Bleeding or Hemorrhaging

This factor of difficulty refers to a blood flow produced by bleeding or hemorrhaging of either the actual tissue to be identified or of adjacent tissues or anatomical structures that are damaged, intentionally or not, during the surgical procedure. It constitutes an extrinsic factor the effects of which are similar to those produced by the aqueous media, and the contamination and deviation of the characteristic spectrum due to the contribution of components of the blood to the laser-generated plume must furthermore be considered. Throughout the text, the term "contaminant" and derivatives thereof must be interpreted as an element that is not related to the biological tissue, among which elements are those produced by a cutting operation or particles suspended in the surrounding atmosphere.

Other Non-Liquid Organic Components

In general, during any surgical or therapeutic operation other components of the tissues may be generated or given off. For example, cutting bone tissue with an Er:YAG laser microscopically volatilizes the tissue and thereby generates particles (also identified as debris) that are deposited in the surgical field.

These particles of the different tissues to be analyzed made it difficult to identify the tissue object of analysis and can trick the system. For this reason it is essential to clear away the debris generated by cutting the tissues with a laser from the surgical field.

Again by way of example, another component that may introduce elements of confusion into the characterization of tissue is the calcinated organic material generated by laser cutting or by cauterizing by means of surgical instruments of another type.

The use of LIBS for identifying tissue is known under laboratory conditions where all the conditions are extremely controlled and work is done on samples of tissues that are processed and handled following the same methodology at all times, and which do not take no have into account circumstances that undoubtedly arise in an actual clinical/surgical situation.

As an example of this phase of preparation, a plurality of "preparation" laser pulses are known to be used for the purpose of removing contaminants and liquids from the surface of the tissue. All cases involve tissues ex vivo without bleeding or liquids on the surface, and in which several measurements are usually taken and then averaged to improve robustness.

There are disclosures in which it is acknowledged that conventional LIBS cannot work in the presence of saline, and for this reason a double-pulse LIBS is used.

According to this technique, a first pulse does not generate a measurable plasma, but rather it serves to produce a small air bubble, known as a cavitation bubble, in the zone of the surface of the material where the pulse strikes. Said cavitation bubble expands rapidly, opening up an air cavity between the surface of the material and the liquid covering it, and this bubble reaches its maximum size, typically between 50 and 200 µs, after the impact of the first pulse. Therefore, when the second pulse strikes the material, it is surrounded by air, so the plasma is generated so as to be as robust as when the sample is not immersed.

Until now, the double-pulse laser has especially be used when a LIBS is to be performed in underwater conditions, such as for the characterization of underwater archeological materials or for the search for hydrocarbons for example.

This technique solves the problem of the abundance of liquid on the sample, but it does not solve the problem of the intrinsic moisture thereof. Likewise, this technique increases the damage produced on the sample by the first pulse by distorting the characteristic measured spectrum.

Another very important drawback is that the method suffers from a lack of robustness and repeatability when there is a presence of liquid having an irregular volume and/or in motion instead of a static water layer. Finally, it is necessary to point out another drawback, which is that the method is sensitive to uncontrollable reductions in detection efficiency due to the lens effect produced by the cavitation bubble.

The technical problem of how to achieve in a process for the discrimination of tissue a plasma plume on a biological tissue subjected to intrinsic moisture conditions, the presence of liquids, the possible presence of contaminating particles, or even the presence of a contaminated atmosphere that is stable and robust and offers good repeatability is considered.

Although one skilled in the art, who is accustomed to working under laboratory conditions, would avoid disturbing the plasma plume generation region to solve the technical problem, the invention solves said problem by disturbing said region by incorporating means generating a gas flow which, in the operating mode, includes the zone of tissue which the laser beam generating the plasma plume strikes.

DESCRIPTION OF THE INVENTION

According to the first inventive aspect, the present invention is a device for the discrimination of biological tissues comprising:
- a first laser emitter configured for emitting in an axial direction X-X' a laser beam capable of causing a plasma plume when striking biological tissue;
- a spectrum reading unit configured for measuring the spectrum of the plasma laser-generated plume beam;
- a central processing unit in communication with the spectrum reading unit configured for receiving the measured spectra and providing an output with a discrimination value in response to the measured spectrum.

The first laser is the component responsible for making a laser beam strike the biological tissue and generating a plasma plume. The laser may utilize, according to several embodiments, a focusing unit concentrating the energy of the laser beam in a region having a smaller area than the section of the beam by increasing the energy intensity per unit of area.

According to a preferred embodiment of the invention, the first laser is a pulsed laser emitting device. The plasma plume emits electromagnetic radiation in a given range of the spectrum and it can be characterized by the intensity of the radiation depending on the wavelength. This spectrum depends on the tissue or the material that has contributed to the formation of the plasma. The occurrence of peak intensities of one or more specific wavelengths may be due to the presence of a specific element or compound.

If the beam strikes the tissue and also any contaminating material, in the best-case scenario, the characteristic spectrum of the plume does not correspond to that of the tissue but rather it is a combination of the spectrum of the tissue and also of the spectrum of the material or materials and elements present that are not related to the tissue. It has been indicated that this situation is in the best-case scenario since the presence of intrinsic moisture, liquids, and/or agents that are not related to the tissue usually give rise to the occurrence of a plasma plume, and therefore it is not even possible to carry out a reading of the spectrum of said plume.

The device includes a spectrum reading unit configured for receiving at least part of the radiation of the plume and thereby determine the spectrum of the plasma plume when the device is in the operating mode.

The discrimination device also incorporates a central processing unit that receives the reading of the radiation spectrum of the plume which is processed for determining a discrimination value that is dependent on the reading.

There may be various discrimination criteria, and some of them will be described as embodiments of the invention.

There is enormous interest in the discrimination of tissues that can be cut during a surgical intervention and of those tissues that have to be preserved intact and therefore cannot be cut. In these cases, the central processing unit establishes a comparison between the spectrum that it receives from the spectrum reading unit with values of the spectrum of tissues that are suitable and not suitable for cutting. The central processing unit thereby provides in the output a first value indicative of a first set of tissues, for example tissues suitable for cutting, and a second value indicative of a second set of tissues, for example tissues not suitable for cutting.

The discrimination of tissues does not necessarily have to be linked to a cutting of the tissue object of discrimination, but rather it is possible to carry out other embodiments where readings are carried out along a path, for example, obtaining information about the tissue along said path.

Among the embodiments, there is also enormous interest in the use of one or more robotic surgical apparatus that control the means described for carrying out readings through established paths in the arm or arms, whether a cut is made or if only discrimination operations are performed.

According to the invention, to prevent distortion in the reading of the spectrum, the device is characterized in that it additionally:
- comprises a blowing unit configured for providing a gas flow, either by means of blowing or by means of suction or by means of blowing and suction, in a region which, in the operating mode, contains the zone of tissue which the laser beam generating the plasma plume strikes.

This blowing unit establishes a gas flow in the region where the laser beam generating the plasma plume strikes, the gas flow entraining primarily the intrinsic moisture which prevents or makes it difficult for the plasma plume to occur, and the elements that are not related to the tissue which may exist and which distort the spectrum of the plasma plume since said flow leaves the tissue free of these other elements, debris, or fluids, such that the plasma plume is generated in a robust and stable manner and only from the tissue.

Although introducing the gas flow is the opposite of what one skilled in the art trying to prevent the sweeping away of the plume or the distortion thereof would do, the invention has been found to solve the problems that are considered because it entrains the intrinsic moisture and the contaminating elements that may exist, but not the laser-generated plume, thereby allowing the reading thereof.

According to a preferred embodiment, the blowing unit acts by blowing a controlled gas (for example stored under pressure) to prevent the blowing from incorporating other contaminating elements or elements that are not related to the tissue. Examples of gas are filtered air or a noble gas to prevent the formation of reaction products with the generated plasma.

According to another embodiment of enormous interest, the blowing unit is configured for blowing a gas flow in the axial direction X-X', i.e., that defined by the laser beam from the first laser emitter. An axial flow not only sweeps away any element that is not related to the tissue, but it additionally protects any optic arranged close to the plasma plume generation region since the projection of any particle when the laser strikes would go against the gas flow and would be stopped or swept away, preventing said particle from reaching the optics that may require the use of a laser.

As indicated, the generation of the plasma plume sometimes generates projections of particles or droplets of liquid that strike, for example, the focusing unit, making it dirty. According to one embodiment, the axial flow perimetrally surrounds the focusing optic and converges once it has gotten past said optic, preventing any projected particle from reaching said focusing unit.

According to other embodiments of the invention, the flow is obtained by suction such that the contaminating elements are removed in a controlled manner.

According to another embodiment of the invention, both blowing and suction are combined, where it allows keeping the optical components protected, for example, and at the same time having the contaminating elements that are removed by means of the flow controlled.

Several embodiments of the invention are described in the detailed description of the invention.

DESCRIPTION OF THE DRAWINGS

These and other features and advantages of the invention will become more evident based on the following detailed description of a preferred embodiment provided only as an illustrative non-limiting example in reference to the attached drawings.

DETAILED DESCRIPTION OF THE INVENTION

Figure 1:
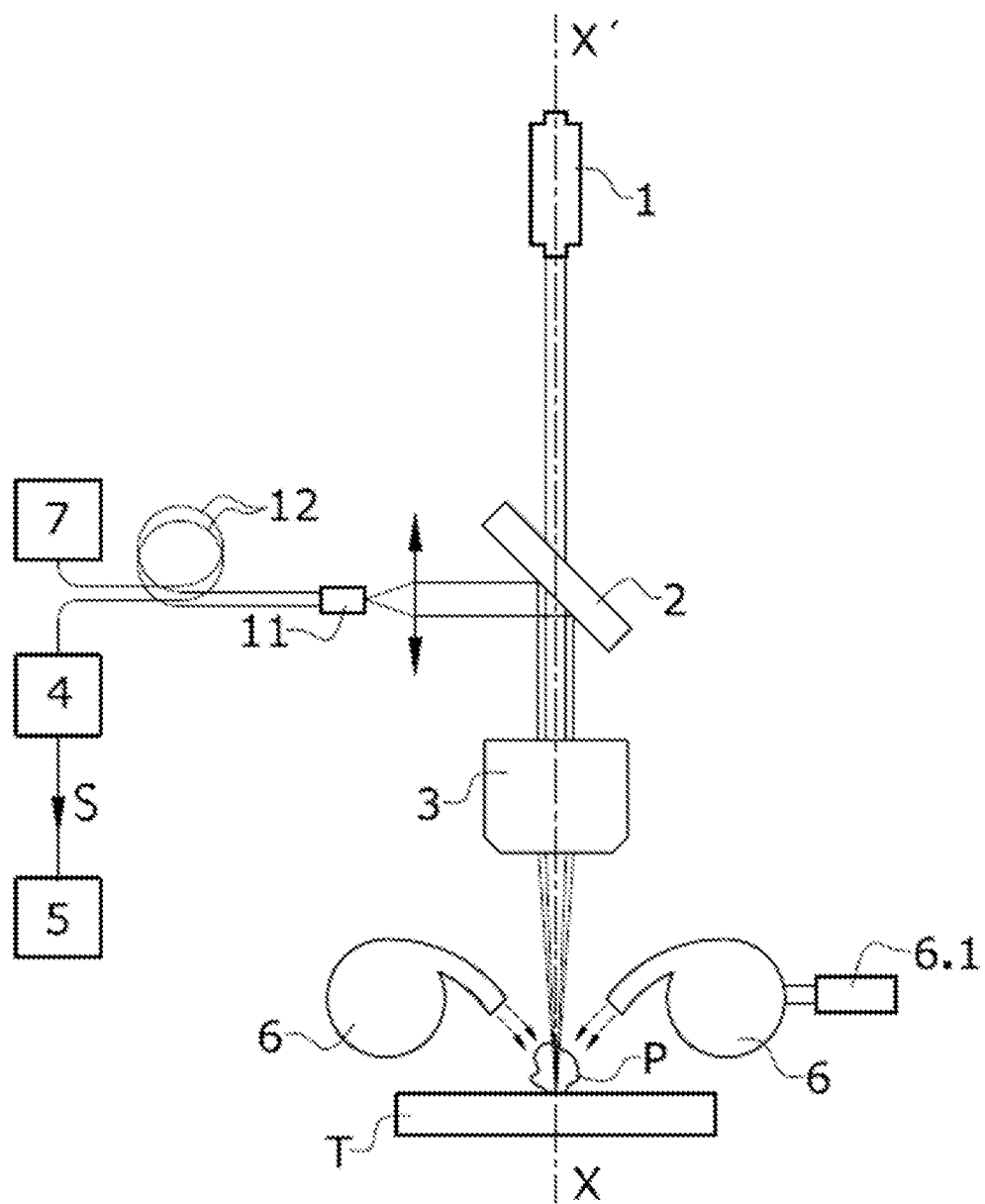
FIG. 1 shows a diagram of a first embodiment of the invention with various elements that allow an efficient use of the discrimination device.

FIG. 1 shows a diagram of a first embodiment of a discrimination device located on a sample of tissue (T). Relative terms such as above, below, to the right, or to the left will be utilized throughout the description. Such terms will refer to the relative positions as they are shown in the drawings, and they must be interpreted with respect to the directions that will be described as reference directions based on elements of the device.

The first reference direction is the direction identified as X-X' established by a first laser emitter (1) which, in the operating mode, emits a laser beam according to this direction X-X' and which is capable of causing a plasma plume (P) when striking biological tissue.

In FIG. 1, the first laser emitter (1) is located in the upper part of the drawing and emits the laser beam towards the sample of tissue (T) located in the lower part and positioned such that it extends according to a surface essentially perpendicular to direction X-X'.

In this embodiment, the device comprises a focusing unit (3) that concentrates the laser beam from the first laser emitter (1) in one point, increasing its energy density. The focal point of the focusing unit (3) is located at focal length (d) and corresponds to a point where the site of the sample of tissue (T) that receives the laser beam for the generation of the plasma plume (P) is located.

In the operating mode, the laser used in this embodiment emits a pulsed beam and the laser is an Nd:YAG-type laser.

When the laser strikes the tissue (T), a plasma plume (P) emitting an electromagnetic radiation with a characteristic spectrum (S) that is dependent on the type of tissue (T) the laser beam strikes is generated.

Part of the radiation of the plasma plume (P), with a characteristic spectrum (S) that is dependent on the tissue (T), is emitted in direction X-X' of the laser beam and is observed by the focusing unit (3) used for concentrating the laser beam.

FIG. 1 depicts the laser beam striking the tissue (T) with two lines representing a narrow beam, and the part of the emission observed by the focusing unit (3) by means of two lines which are shown more separated from one another and define a wider beam, the return beam.

This return beam returning through the focusing unit (3) according to direction X-X' is what is used for taking the measurement of the characteristic spectrum (S).

The beam emitted by the first laser emitter (1) goes through a beam combiner (2) which is transparent for this beam. The beam combiner (2) is shown in the oblique position, specifically at 45°, since this beam combiner (2) is not transparent for the return beam returning from the plasma plume (P). The return beam is reflected to the left, reaching a spectrum reading unit (4).

The spectrum reading unit (4) comprises sensors determining the characteristic spectrum (S) of the plasma plume (P), and it is transmitted to a central processing unit (5) which establishes, under a discrimination criterion, a discrimination output value in response to the characteristic measured spectrum (S).

FIG. 1 shows an interface optic (11) that allows introducing the return beam into an optical fiber (12) for introducing same into the spectrum reading unit (4).

This same figure schematically shows a blowing unit (6) which blows a gas flow onto the region where the plasma plume (P) is formed for sweeping away the intrinsic moisture or any contaminating element located on the sample of tissue (T) or in the surrounding atmosphere.

In the depicted diagram, two blowers have been symmetrically arranged to configure an axial flow in the area surrounding the plasma plume (P). Nevertheless, other embodiments are possible by combining blowing, suction, or both either simultaneously or in an alternating manner. Even though the blowing unit (6) is an essential feature of the invention, some later figures do not show the blowing unit (6) so as to make it easier to see the lines and objects located close to the position where the blowing unit (6) is located. The absence of this graphical representation does not mean that this blowing unit (6) is not there.

Figure 2:
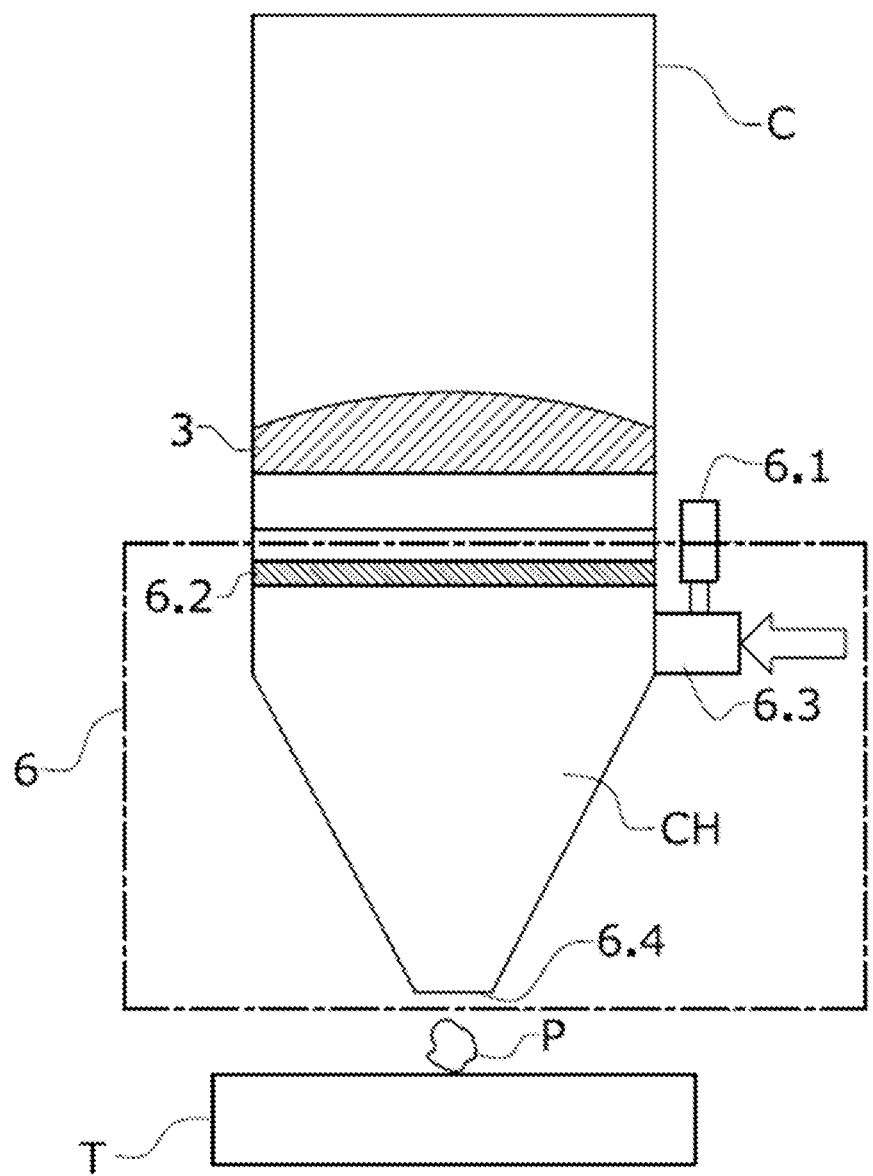
FIG. 2 shows an embodiment of the part that allows the blowing on the discrimination region.

FIG. 2 shows an embodiment of the blowing unit (6) formed by a chamber (CH) comprising an air inlet (6.3) to raise the pressure inside said chamber (CH) with an overpressure with respect to atmospheric pressure.

The chamber (CH) of the blowing unit (6) has a window (6.2) formed by a transparent plate which allows the passage of the laser beam and of the return beams and which protects the focusing unit (3). The transparent plate forming the window (6.2) establishes the pressurized closure of the chamber in the direction of the focusing unit (3).

In the lower part of the chamber (CH), in the part opposite the window (6.3), there is arranged a nozzle (6.4) that allows the outflow of the air towards the sample of tissue (T) and the region where the plasma plume (P) is generated when the laser beam strikes.

According to this embodiment, an air jet in the axial direction X-X' of the laser beam generating the plasma plume (P) is achieved, and said air jet prevents the entry of particles projected from the region where the plasma plume (P) is generated towards the window (6.2) and/or towards the focusing unit (3).

In this same embodiment, a casing (C) housing at least the focusing unit (3) and connected to the blowing unit (6) in its lower part and to the first laser emitter (1) in the upper part, opposite the lower part, has been depicted.

This same casing (C) according to this embodiment has means for being connected with the interface optic (11) for connecting with the optical fiber (12), forming a protected internal space.

FIG. 1 and FIG. 2 schematically show a mist generating module (6.1) for incorporating a mist into the gas flow for given embodiments, where the atmosphere in which the plasma plume (P) is created requires it. In this particular case, the atmosphere where the plasma plume (P) is generated is controlled, and therefore so is the influence of the mist on the characteristic measured spectrum (S).

The existence of a spectrum reading unit (4) transmitting the characteristic measured spectrum (S) to the central processing unit (5) in charge of providing an output with a discrimination value in response to the measured spectrum (S) has been described.

This discrimination value, in response to or depending on the characteristic measured spectrum (S), is different depending on the discrimination criterion applied.

A first embodiment with respect to the discrimination criterion pre-establishes one or more wavelength values as values on which the comparison with the characteristic measured spectrum (S) is carried out. The simplest case consists of using a single wavelength $\lambda_1$ on which a threshold value $M_1$ is also pre-established.

If the amplitude of the characteristic measured spectrum (S) in wavelength $\lambda_1$ exceeds the threshold value $M_1$, then the output value as a result of the discrimination operation is a first value, and if it is not exceeded, the output value is a second value.

In this embodiment, the value of the wavelength $\lambda_1$ corresponds to a wavelength in which there is a peak intensity in the characteristic measured spectrum (S) insofar as the tissue (T) on which the plasma plume (P) is formed contains a characteristic component of the tissue to be discriminated. A value that is a good candidate for choosing the wavelength $\lambda_1$ is a characteristic wavelength of the characteristic component of the tissue to be discriminated, in other words, it is a wavelength in which that component shows a peak intensity, but which does not correspond to a peak intensity for any of the components of the tissue that are not to be discriminated.

Another more robust embodiment establishes a plurality of wavelengths $\lambda_i$, i=1, ..., n, for which n threshold values $M_i$, i=1, ..., n, are predetermined, such that the condition of being wavelengths in which there is a high intensity value greater than its pre-established threshold value when the tissue is the tissue (T) to be discriminated and which do not occur when the tissue (T) is different from tissue to be discriminated is verified.

A second embodiment for carrying out the discrimination using the central processing unit (5) provides a value with more information as it corresponds to a value identifying a specific tissue.

The central processing unit (5) has stored internally or externally a plurality of spectra ($E_1$, $E_2$, $E_3$, ..., $E_m$) corresponding to the plasma generated by the first laser emitter (1) in a plurality of different biological tissues ($T_1$, $T_2$, $T_3$, ..., $T_n$).

When the central processing unit (5) receives the characteristic measured spectrum (S), it compares it with the plurality of spectra ($E_1$, $E_2$, $E_3$, ..., $E_m$), determining for each of them a value that represents the degree of similarity. An example of a measurement of the degree of similarity consists of predefining a rule in which the difference in spectra is measured. A particular case of a rule establishes the difference in absolute value of a sample with respect to values in a pre-established set of wavelengths.

Of all the comparisons, the one providing the highest degree of similarity corresponds to the spectrum which in turn corresponds to the identified biological tissue, and this is the output provided by the central processing unit (5) as a discrimination value.

The central processing unit (5) can provide more values of identified tissues, for example ordered by their degree of similarity.

In any of the cases, the spectrum (S) that is read can be subjected to a pre-processing, for example for noise filtering. Then pre-processed spectrum is the object of comparison.

The discrimination value delivered by the central processing unit (5) corresponds to a point of the tissue (T) on which the plasma plume (P) has been generated.

According to one embodiment, the discrimination device carries out a plurality of laser emissions with the first laser emitter (1) in a plurality of points of the tissue (T), and determines the discrimination value from the plasma plume (P) that is generated.

This plurality of measurements determines a plurality of discrimination values distributed in an area. A specific way of carrying out these measurements of the discrimination values is by utilizing a discretization grid, which gives rise to a regular distribution of the points that are distributed in rows and columns.

Figure 3:
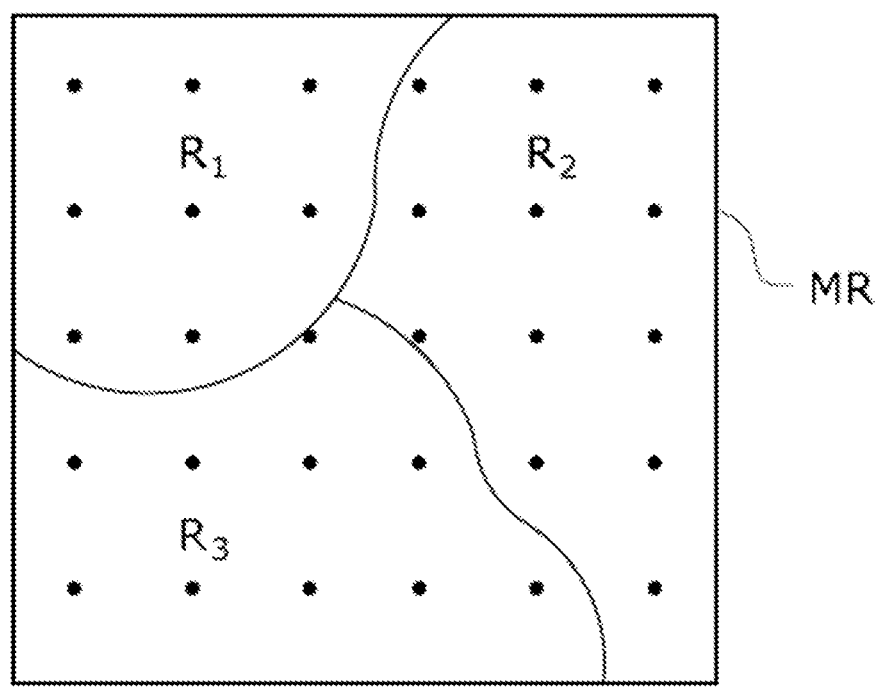
FIG. 3 shows an area of the tissue to be discriminated on which a plurality of measurements has been taken for determining a discrimination value. The points distributed according to a regular rectangular grid are the points where the discrimination operation has been performed. The identification of three areas which correspond to three different discrimination values has been determined with a subsequent processing of these values.

FIG. 3 shows a rectangular area on which a set of readings has been carried out for the determination of a discrimination value with the prior generation of a plasma plume (P), these readings being distributed according to a rectangular grid and graphically represented by means of points distributed in rows and columns.

With these values, the central processing unit (5) determines regions of the sampled area with discrimination values which correspond to the same discrimination value. There are numerical libraries which, based on a discrete function, establish regions in the domain of the discrete function which correspond to the one or more values the function takes.

A particular way of carrying out this identification of regions, as merely an exemplary embodiment, consists of constructing, by interpolation, a continuous scalar function with the domain of the function defined in the area where the sampled values are presented, and then determining the level curves of the continuous function which correspond to the different discrimination values.

The domain on which the plurality of measurements has been taken and the subsequent determination of regions which correspond to the values the result of the discrimination takes is referred to as the map of regions (MR), and this can be seen by way of example in FIG. 3. In this specific example, discrimination has been carried out in which the device returns as the discrimination value an identifier of a given tissue (T). With the values of the tissue, the central processing unit (5) has established three different regions, one for each tissue (T) that is identified.

As a specific case, this map of regions (MR) is important in the context of working in a surgical field since it allows identifying those regions of the tissue (T) where a cut can be made and those regions of the tissue in which a cut cannot be made.

In the particular case of the map of regions (MR) shown in FIG. 3, for example, regions R1 and R2 correspond to tissues (T) that can be cut and the region R3 corresponds to a tissue that cannot be cut.

Several embodiments which allow the interaction of the user with the device by switching the mode in which said user receives the information of the map of regions (MR) are described in the context of the invention.

Figure 4:
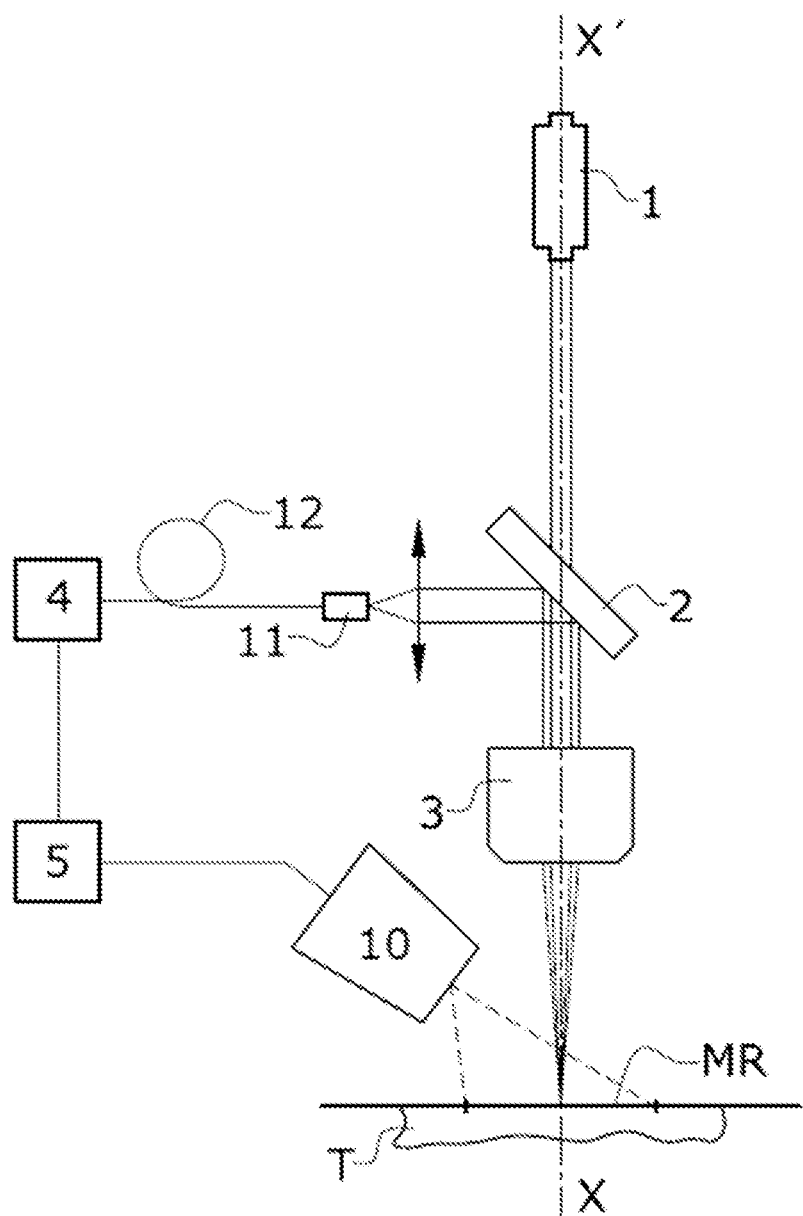
FIG. 4 shows an embodiment of the invention where a map of regions obtained after the determination of a plurality of discrimination values in a surgical field is provided to the user by means of a projector projecting the map of regions onto the surgical field.

As shown in FIG. 4, in a first embodiment with respect to the mode of the user receiving the map of regions (MR), the discrimination device incorporates a projector (10) used for projecting the image of the map of regions (MR) onto the area where the plurality of measurements has been taken.

Once calibrated, the projector (10) is configured so that the points of the map of regions (MR) which correspond to the points where the reading has been carried out for preparing the map of regions (MR) coincide with the points of the tissue where the plasma plume (P) has been generated, corresponding to its point of the map of regions (MR).

According to this embodiment, the user sees on the actual surgical field which tissue can be cut and which tissue cannot be cut.

A specific way of projecting the map of regions (MR) onto the surgical field is by assigning different colors for each type of tissue (T) identified in the discrimination process, for example using bolder colors, such as red, for those tissues (T) that must not be cut.

Figure 5:
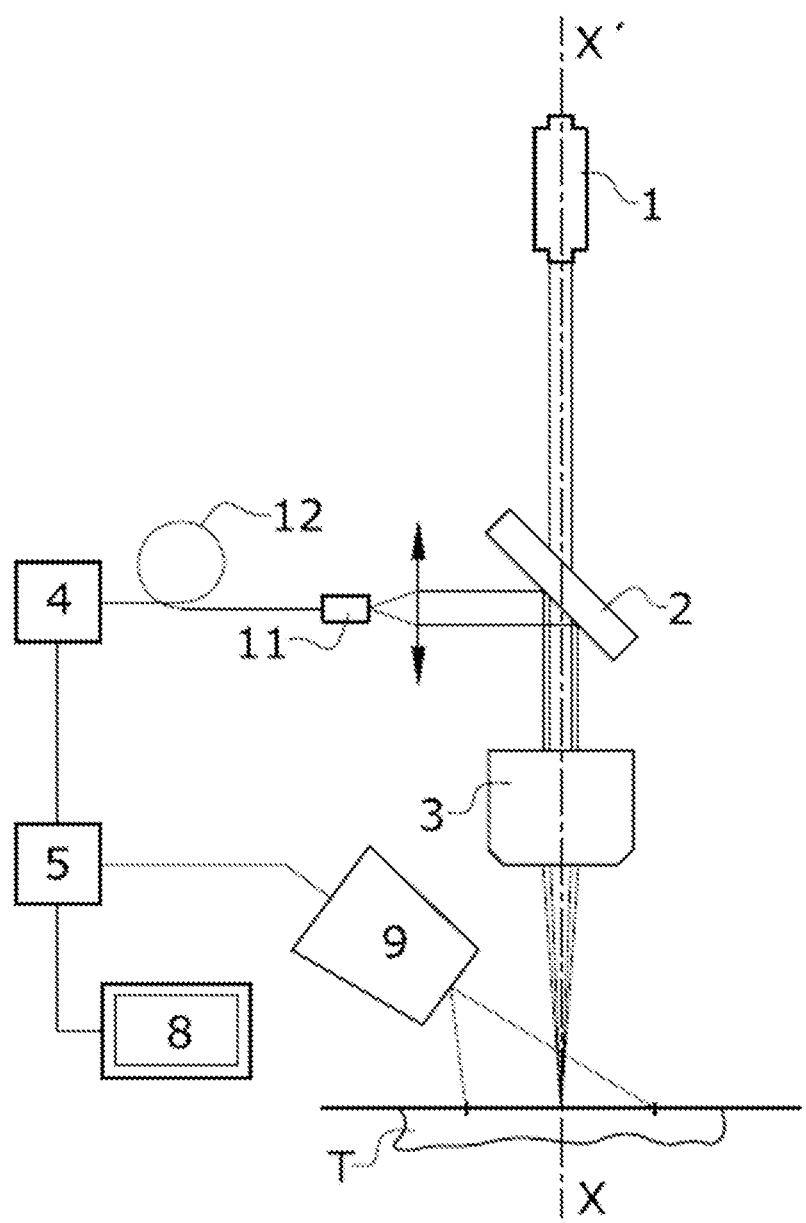
FIG. 5 shows an embodiment of the invention where a map of regions obtained after the determination of a plurality of discrimination values in a surgical field is provided to the user by means of a display device which combines the image of the surgical field and the map of regions.

A second embodiment with respect to the way of providing the information of the map of regions (MR) to the user is shown in FIG. 5. The discrimination device comprises a camera (9) for capturing the image of the surgical field on which the plurality of measurements has been taken. The central processing unit (5) determines the map of regions (MR) and generates an image resulting from combining the image captured by camera (9) and the image which corresponds to the map of regions (MR).

A specific way of combining both images applies a degree of transparency to the image of the map of regions (MR) and superimposes it on the image captured by the camera (9). The result is an image that shows the surgical field with the map of regions (MR) superimposed thereon.

The discrimination device additionally comprises an image display device (8) making the combined or superimposed image accessible to the user. Examples of display devices (8) are monitors, or for example a display unit configured in the form of glasses which allow for a more immersive experience for the user.

Another embodiment combines a discrimination device according to any of the examples described with a cutting apparatus (7) that is or is not able to cut, i.e., of being activated and deactivated, such that the user is capable of cutting the tissue (T) about which discrimination information has been obtained, identifying it as being suitable for being cut.

The switching between activated and deactivated can be automatic or by hand. Examples of activation by hand are those in which the user has a map of regions (MR) and is capable of seeing which regions are suitable for cutting, with the user activating the cutting when he/she sees that it is viable.

An example of automatic activation or deactivation is one in which cutting is performed on previously discriminated regions, and with respect to said regions a discrimination result that identifies the tissue (T) as being suitable for cutting has been obtained, such that once the discrimination device determines that a measurement gives as a discrimination result that the tissue is not suitable for being cut, the central processing unit (5) deactivates the cutting apparatus (7).

Figure 6:
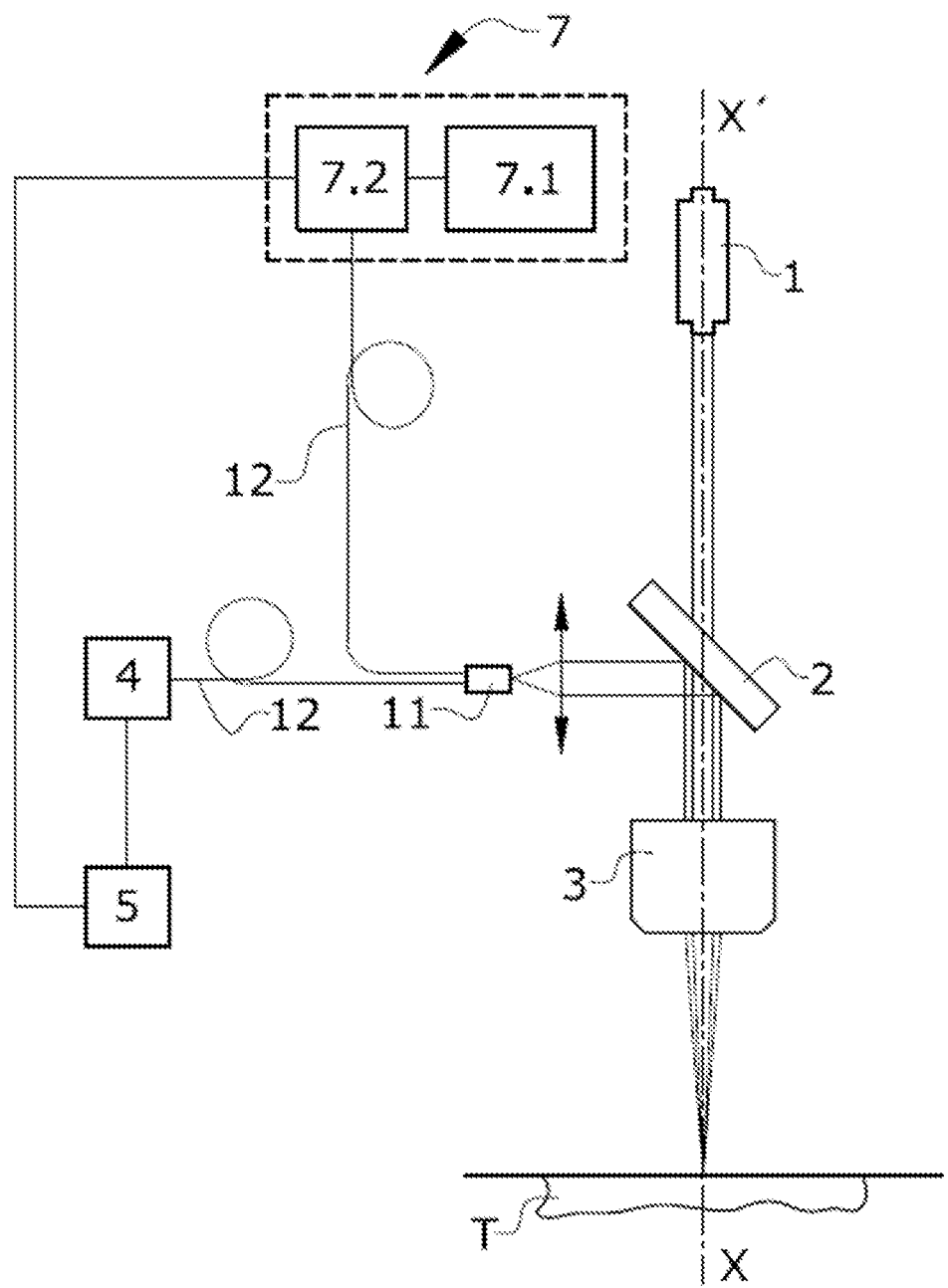
FIG. 6 shows an embodiment of the invention which, in addition to carrying out the discrimination of tissues, incorporates means for carrying out a selective cutting that is dependent on the result of the discrimination.

FIG. 6 shows an embodiment in which the cutting apparatus (7) comprises a second laser emitter (7.2) with enough power to cause the cutting of the biological tissue (T).

Even though FIG. 6 shows, identified as the cutting apparatus (7) using discontinuous lines, the second laser emitter (7.2) and a manual actuator (7.1) which allows deactivating the second laser emitter (7.2) by the actuation of the user, the cutting apparatus (7) may involve more components. In the embodiment shown in FIG. 6, the laser beam emitted by the second laser emitter (7.2) also utilizes the interface optic (11), the beam combiner (2), and the focusing unit (3) used by the discrimination device.

FIG. 6 shows how the second laser emitter (7.2) emits a laser beam through an optical fiber (12) reaching the same interface optic (11) used for the reading of the characteristic spectrum (S).

According to one embodiment, the laser emission that performs the cutting is carried out at the point where the discrimination value has previously been obtained.

According to a second embodiment, for example by means of the second cutting laser (7.2), the cutting is performed along a path and it stops when it reaches on the surgical field a region close to a region identified as not suitable for cutting.

In other words, the cutting performed by the cutting apparatus (7) does not necessarily have to be located on the X-X' axis. Another example of cutting apparatus (7) is a scalpel which can be activated by hand or automatically. In this case, the activation or deactivation of the cutting apparatus (7) lowers or raises the cutting blade of the scalpel, respectively.

FIG. 6 shows a manual actuator (7.2) for a cutting apparatus that performs a cutting operation by hand, and the same figure shows how the central processing unit (5) is in communication with the cutting apparatus (7) for carrying out the activation or deactivation of the cutting automatically depending on if the cutting point is in a region identified, by means of a prior discrimination operation, as suitable or not suitable for cutting, respectively.

According to another embodiment, the cutting point on the tissue (T) is established at a point of the tissue (T) spaced apart from the point where the first laser emitter generates the plasma plume (P). A specific example of this configuration consists of performing the cutting at a point of a previously determined path located behind the point of the same path where the reading that has given rise to the discrimination was carried out. It is thereby assured in a continuous cutting movement that the identification of a region not suitable for cutting is carried out before the cutting reaches said region that is not suitable.

In all these cases, when referring to a point, said point corresponds to geometric places located on the surface of the biological tissue (T) when the discrimination device is in the operating position with respect to the tissue (T) to be discriminated. In other words, in all cases they are points of the surface of the biological tissue (T). In particular, these points are those which are located in the area referred to as surgical field or in a map of regions (MR).

In these embodiments, the combiner (2) allows the reflection of both the cutting laser beam (7.2) and the return beam coming from the plasma plume (P).

According to one embodiment, the beam combiner (2) is a perforated mirror. The perforation allows the passage of the beam coming from the first laser emitter (1) the diameter of which is small. The area of mirror surrounding the perforation is the area where both the return beam coming from the plasma plume (P) and the cutting laser beam, if there is one, are reflected. In this case, the cutting beam will have a larger diameter than the perforation to enable being reflected by the mirror either towards the cutting point or towards the focusing unit (3).

In this described embodiment, the configuration of the device is such that:
the connection between the second laser emitter (7.2) and a point of emission of the laser beam towards the mirror (2);
the connection between the spectrum reading unit (4) and a point of observation of the plasma plume (P) through the mirror (2); or both connections;
are established by means of a wave guide.

According to one embodiment, the discrimination device according to any of the examples described above, with or without a cutting apparatus (7), is installed in a robotic surgical apparatus, for example configured in the form of a robotic arm, which allows the movement of the discrimination device connected to said surgical apparatus. According to one embodiment, the movement of the device is according to paths that are pre-established either by the central processing unit (5) or by means of another separate central processing unit. According to another embodiment, the movement of the discrimination apparatus by means of the surgical apparatus is controlled directly by the user, for example by means of a joystick-type input device.

In any of the embodiments, the first laser emitter (1), the second laser emitter (7.2), or both, are pulsed lasers.

The invention claimed is:

1. A device for the discrimination of biological tissues comprising:
    a first laser emitter configured for emitting in an axial direction X-X' a laser beam capable of causing a plasma plume when striking biological tissue;
    a spectrum reading unit configured for measuring a spectrum of the plasma plume generated by the laser beam;
    a central processing unit in communication with the spectrum reading unit configured for receiving the measured spectrum measured by the spectrum reading unit and for providing an output with a first discrimination value in response to the measured spectrum;
    a blowing unit configured for providing a gas flow, either by blowing, by suction, or by blowing and suction, in a region which, in an operating mode, contains a zone of tissue which the laser beam generating the plasma plume strikes;
    characterized in that the blowing unit is configured for adapting the flow such to leave the tissue free of any fluids, debris, and other elements not related to the tissue; and
    wherein the central processing unit is configured for continuously executing the following instructions:
    i. receiving the measured spectrum from the spectrum reading unit;
    ii. comparing the received measured spectrum with a plurality of previously stored spectra ($E_1, E_2, E_3, \ldots, E_m$) corresponding to a plurality of light respectively emitted by a plurality of plasma generated by the first laser emitter in a plurality of different biological tissues ($T_1, T_2, T_3, \ldots, T_n$) respectively,
    iii. determining a biological tissue ($T_i$), of the plurality of different biological tissues, that have a spectrum ($E_i$), of the plurality of previously stored spectra, that is closest to the received measured spectrum;
    iv. providing as the first discrimination value, an identification of the biological tissue ($T_i$) determined in the preceding step.

2. The device according to claim 1, wherein the blowing unit is oriented so as to provide the gas flow in the axial direction X-X'.

3. The device according to claim 1, additionally comprising a focusing unit for the focusing of the laser beam according to the axial direction X-X' at a given focal length.

4. The device according to claim 1, wherein said device is configured for carrying out a plurality of measurements, using the first laser emitter and the spectrum reading unit, of the first discrimination value in a region of a field of operation, and wherein the central processing unit is configured for determining a map of regions with the plurality of measurements, this map of regions comprising at least an area or areas of said region of the field of operation which correspond to a second discrimination value and an area or areas of said region of the field of operation which correspond to a third discrimination value.

5. The device according to claim 4, comprising:
an image projector configured for projecting an image comprising at least the map of regions generated by the central processing unit.

6. The device according to claim 4, comprising:
a camera configured for capturing an image of the field of operation, and
a image display device;
wherein the central processing unit is configured for superimposing an image with the map of regions on the image provided by the camera, and sending a superimposition of the images to the image display device so it can be viewed.

7. A selective biological tissue ablation device comprising:
a device for the discrimination of biological tissues according to claim 1;
a cutting apparatus, that can be activated and deactivated either automatically or by hand, configured for cutting into the tissue in which the device for the discrimination of biological tissues carries out the discrimination.

8. The device according to claim 7, wherein the cutting apparatus is configured for automatically deactivating the cutting when the device for the discrimination of biological tissues provides an output with the second discrimination value and activating the cutting when the device for the discrimination of biological tissues provides an output with the third discrimination value.

9. The device according to claim 7, wherein the cutting apparatus comprises a second laser emitter.

10. The device according to claim 9, wherein the second laser emitter is configured for emitting a second laser beam such that the path of the second laser beam goes through a beam combiner, for combining the laser beam from the first laser emitter and the second laser beam from the second laser emitter, for subsequently passing the paths of both beams through a focusing unit for the focusing of a laser beam according to the axial direction X-X' at a given focal length.

11. The device according to claim 10, wherein the beam combiner is a perforated mirror, and:
a connection between the second laser emitter and a point of emission of the laser beam towards a mirror;
a connection between the spectrum reading unit and a point of observation of the plasma plume through the mirror; or
both connections;
are established by means of a wave guide.

12. A device comprising:
a robotic surgical apparatus;
a device according to claim 1 connected to at least one part of the robotic surgical apparatus.

* * * * *